US012588821B2

(12) United States Patent
Lee et al.

(10) Patent No.: US 12,588,821 B2
(45) Date of Patent: Mar. 31, 2026

(54) BODY TEMPERATURE ESTIMATION SYSTEM AND METHOD BASED ON ONE-CHANNEL TEMPERATURE SENSOR

(71) Applicants: KOREA ELECTRONICS TECHNOLOGY INSTITUTE, Seongnam-si (KR); Namsung InfraNet Co., Ltd., Seoul (KR)

(72) Inventors: Min Goo Lee, Seoul (KR); Yong Kuk Park, Seoul (KR)

(73) Assignees: KOREA ELECTRONICS TECHNOLOGY INSTITUTE, Seongnam-si (KR); NAMSUNG INFRANET CO., LTD., Seoul (KR)

( * ) Notice: Subject to any disclaimer, the term of this patent is extended or adjusted under 35 U.S.C. 154(b) by 608 days.

(21) Appl. No.: 18/053,902

(22) Filed: Nov. 9, 2022

(65) Prior Publication Data
US 2024/0148254 A1 May 9, 2024

(51) Int. Cl.
    *A61B 5/01* (2006.01)
    *A61B 5/00* (2006.01)
    (Continued)
(52) U.S. Cl.
    CPC .............. *A61B 5/01* (2013.01); *A61B 5/6833* (2013.01); *A61B 5/7246* (2013.01); *G01K 1/143* (2013.01);
    (Continued)
(58) Field of Classification Search
    CPC ....... A61B 5/01; A61B 5/6833; A61B 5/7246; A61B 2562/0271; A61B 5/02055; G01K 1/143; G01K 13/20
    See application file for complete search history.

(56) References Cited

U.S. PATENT DOCUMENTS 11,517,203 B2 * 12/2022 Reifman ................ G16H 50/30
2018/0184908 A1 * 7/2018 Meyerson ............ A61B 5/6833
(Continued)

FOREIGN PATENT DOCUMENTS

KR       10-1855573 B1    5/2018
KR       20210121359    *  3/2020
KR    10-2021-0121360 A    10/2021

OTHER PUBLICATIONS

Office Action issued on Aug. 22, 2025, for corresponding Singapore Patent Application No. 10202251411X (5 pages).
(Continued)

*Primary Examiner* — Eric F Winakur
*Assistant Examiner* — Noah M Healy
(74) *Attorney, Agent, or Firm* — Hauptman Ham, LLP

(57) ABSTRACT
A body temperature estimation system and method based on a one-channel temperature sensor are proposed for estimating the body temperature of a target person considering a change in the space temperature or a change in the skin temperature according to a change in the space temperature when continuously measuring the body temperature. The body temperature estimation system may include a temperature measurement unit and a body temperature estimation unit. The temperature measurement unit is attached to a skin of the target person and measures a skin temperature at regular intervals. The body temperature estimation unit estimates a current body temperature, based on an average body temperature measured at the regular intervals and the skin temperature received from the temperature measurement unit, by reflecting the average body temperature, the skin temperature, a difference value (h) of the skin temperature, and a change amount (h') of the skin temperature difference value.

12 Claims, 13 Drawing Sheets

(51) Int. Cl.
    *G01K 1/143*       (2021.01)
    *G01K 3/10*        (2006.01)
    *G01K 13/20*      (2021.01)

(52) U.S. Cl.
    CPC ............... *G01K 3/10* (2013.01); *G01K 13/20*
    (2021.01); *A61B 2562/0271* (2013.01)

(56)              References Cited

U.S. PATENT DOCUMENTS

| | | |
|---|---|---|
| 2021/0096032 A1 | 4/2021 | Lane et al. |
| 2021/0106238 A1 | 4/2021 | Strasser et al. |
| 2021/0204819 A1 | 7/2021 | Kim et al. |
| 2022/0358372 A1* | 11/2022 | Nishikawa ............. G06N 20/20 |

OTHER PUBLICATIONS

Office Action issued on Jul. 14, 2025, for U.S. Appl. No. 18/053,906 (26 pages).

* cited by examiner

FIG. 8

Start

Wearable temperature patch attached to target
person's skin measures external temperature and
skin temperature at regular intervals, and
body part thermometer measures body temperature
of target person at regular intervals — S10

Management terminal estimates current body
temperature through correlation modeling
between measured body temperature and
at least one of measured skin temperature
and measured external temperature — S30

End

FIG. 9

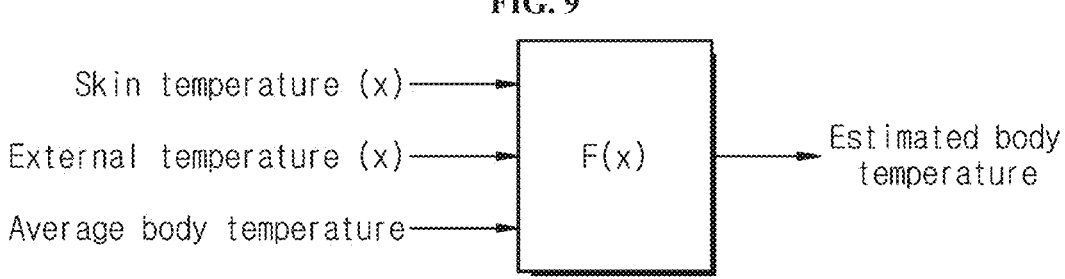

Skin temperature (x) ⟶
External temperature (x) ⟶  F(x)  ⟶ Estimated body
Average body temperature ⟶          temperature

FIG. 11

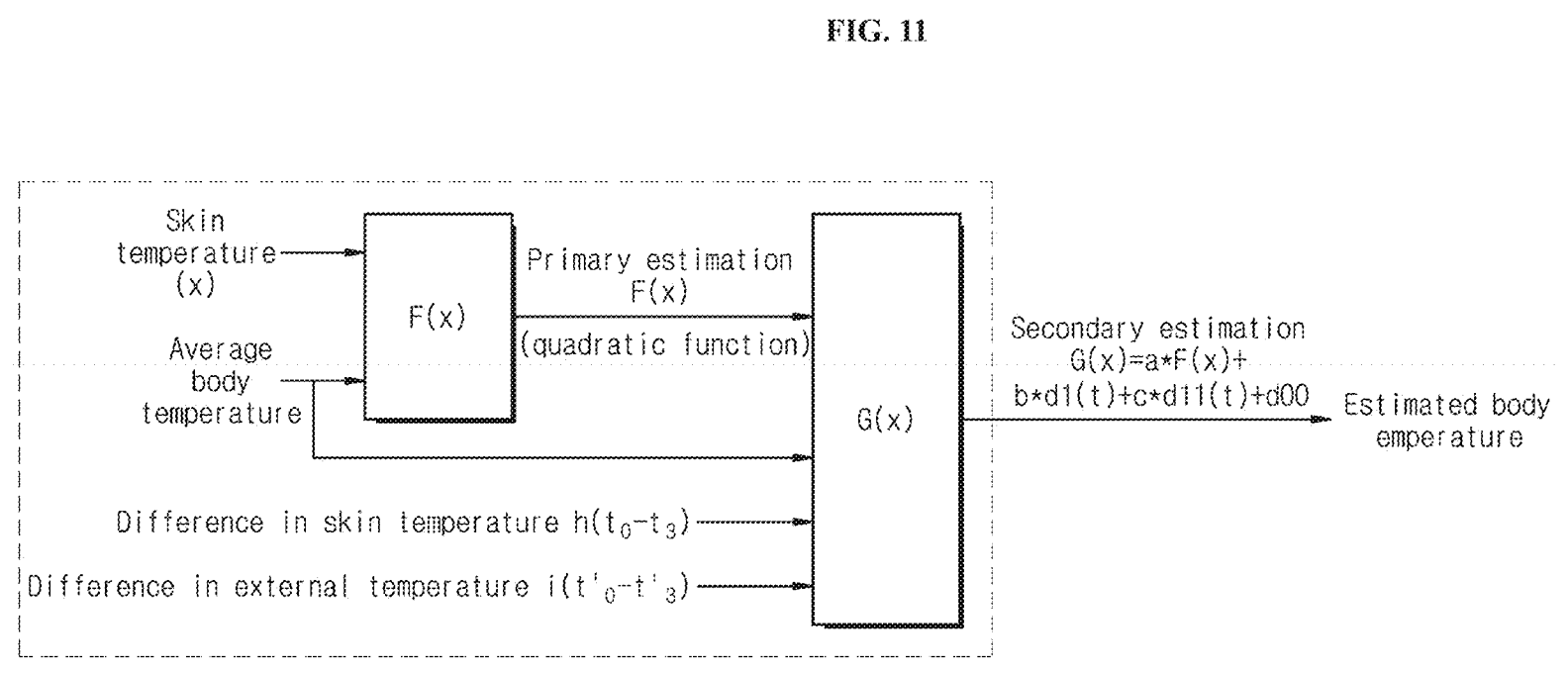

Skin temperature (x)

Average body temperature

F(x)

Primary estimation F(x) (quadratic function)

Difference in skin temperature $h(t_0-t_3)$

Difference in external temperature $i(t'_0-t'_3)$

G(x)

Secondary estimation $G(x)=a*F(x)+b*d1(t)+c*di1(t)+d00$

Estimated body temperature

FIG. 14

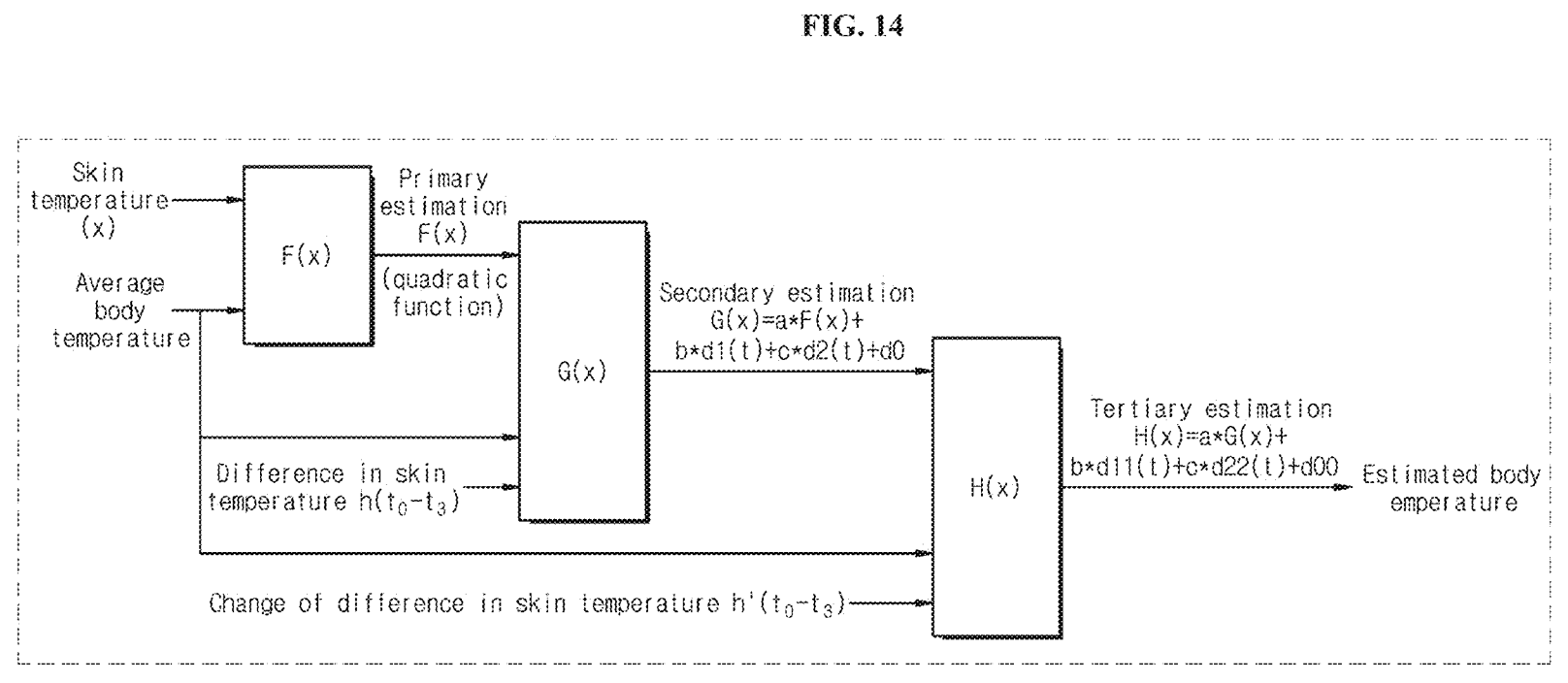

Skin temperature (x)

Average body temperature

Difference in skin temperature h(t₀-t₃)

Change of difference in skin temperature h'(t₀-t₃)

F(x)

Primary estimation F(x) (quadratic function)

G(x)

Secondary estimation
G(x)=a*F(x)+
b*d1(t)+c*d2(t)+d0

H(x)

Tertiary estimation
H(x)=a*G(x)+
b*d11(t)+c*d22(t)+d00    Estimated body temperature

FIG. 15

|  | A | C | E | K |
|---|---|---|---|---|
| 1 | Measure time | External | Chest skin | CORE |
| 2 | AM 8:40 | 30.64 | 33.87 | 36.38 |
| 3 | AM 9:18 | 31.63 | 34.15 | 36.46 |
| 4 | AM 9:41 | 30.89 | 34.33 | 36.36 |
| 5 | AM 10:10 | 31.43 | 34.48 | 36.26 |
| 6 | AM 10:36 | 30.35 | 33.94 | 36.28 |
| 7 | AM 11:04 | 30.34 | 33.91 | 36.36 |
| 8 | AM 11:34 | 31.1 | 34.07 | 36.34 |
| 9 | AM 12:03 | 29.75 | 34.06 | 36.4 |
| 10 | PM 12:31 | 29.09 | 33.82 | 36.44 |
| 11 | PM 1:03 | 29.57 | 33.82 | 36.36 |
| 12 | PM 1:33 | 32.92 | 34 | 36.34 |
| 13 | PM 2:02 | 31.85 | 34.48 | 36.4 |
| 14 | PM 2:36 | 30.64 | 34.21 | 36.52 |
| 15 | PM 3:04 | 31.28 | 34.66 | 36.42 |
| 16 | PM 3:36 | 29.61 | 33.4 | 36.46 |
| 17 | PM 4:18 | 26.13 | 31.91 | 36.54 |
| 18 | PM 4:35 | 28.68 | 32.7 | 36.44 |
| 19 | PM 5:03 | 29.27 | 32.8 | 36.44 |
| 20 | PM 5:34 | 31.15 | 33.75 | 36.52 |
| 21 | PM 5:55 | 30.75 | 33.95 | 36.58 |
| 22 | PM 6:57 | 30.41 | 34.16 | 36.68 |
| 23 | PM 7:31 | 32.12 | 34.51 | 36.78 |
| 24 | PM 7:54 | 31.66 | 34.57 | 36.96 |
| 25 | PM 8:24 | 31.5 | 35.11 | 36.72 |
| 26 | AM 8:52 | 30.75 | 33.62 | 36.34 |
| 27 | AM 9:28 | 31.5 | 33.71 | 36.46 |
| 28 | AM 9:50 | 30.61 | 33.63 | 36.42 |
| 29 | AM 10:14 | 31.03 | 33.88 | 36.54 |
| 30 | AM 10:45 | 31.19 | 34.06 | 36.38 |
| 31 | AM 11:09 | 29.35 | 33.49 | 36.44 |
| 32 | AM 11:38 | 30.31 | 34.08 | 36.5 |
| 33 | PM 12:07 | 30.16 | 34.12 | 36.62 |
| 34 | PM 12:33 | 31.3 | 34.31 | 36.72 |
| 35 | PM 1:05 | 31.84 | 34.64 | 36.82 |
| 36 | PM 1:39 | 31.46 | 34.48 | 36.66 |
| 37 | PM 2:05 | 31.35 | 34.64 | 36.66 |
| 38 | PM 2:50 | 31.07 | 34.3 | 36.68 |
| 39 | PM 3:09 | 30.78 | 34.1 | 36.6 |
| 40 | PM 3:36 | 27.29 | 33.18 | 36.5 |
| 41 | PM 4:15 | 30.61 | 34.48 | 36.8 |

. . .

| 360 | PM 7:32 | 30.26 | 34.82 | 36.86 |
|---|---|---|---|---|
| 361 | PM 7:5 | 31.72 | 34.78 | 36.82 |
| 362 | AM 9:24 | 30.6 | 33.54 | 36.56 |
| 363 | AM 9:52 | 30.21 | 33.85 | 36.68 |
| 364 | AM 10:23 | 31.92 | 34.7 | 36.86 |
| 365 | AM 11:04 | 30.63 | 33.95 | 36.6 |
| 366 | AM 11:28 | 30.69 | 34.04 | 36.62 |
| 367 | AM 11:55 | 31.6 | 34.72 | 36.5 |
| 368 | PM 12:27 | 29.25 | 33.73 | 36.5 |
| 369 | PM 1:04 | 30.28 | 34.01 | 36.74 |
| 370 | PM 1:39 | 32.76 | 34.66 | 36.64 |
| 371 | PM 2:06 | 33.68 | 35.22 | 36.69 |
| 372 | PM 2:32 | 30.65 | 34.56 | 36.94 |
| 373 | PM 3:04 | 32.21 | 34.82 | 36.78 |
| 374 | PM 3:38 | 32.82 | 34.96 | 36.78 |
| 375 | PM 4:18 | 28.95 | 34.42 | 36.7 |
| 376 | PM 4:37 | 32.57 | 34.81 | 36.74 |
| 377 | PM 5:08 | 30.21 | 34.59 | 36.82 |
| 378 | PM 5:39 | 32.98 | 35.04 | 36.8 |
| 379 | PM 6:05 | 30.77 | 34.47 | 36.48 |
| 380 | AM 9:23 | 31.61 | 34.51 | 36.82 |
| 381 | AM 9:59 | 32.7 | 35.24 | 36.68 |
| 382 | AM 10:24 | 31.31 | 34.84 | 36.62 |
| 383 | AM 11:12 | 31.35 | 34.55 | 36.54 |
| 384 | AM 11:39 | 31.11 | 34.36 | 36.48 |
| 385 | AM 11:53 | 31.36 | 34.81 | 36.62 |
| 386 | PM 12:29 | 33.19 | 35.11 | 36.52 |
| 387 | PM 1:05 | 33.33 | 35.55 | 36.7 |
| 388 | PM 1:35 | 33.92 | 35.81 | 37.04 |
| 389 | PM 2:04 | 33 | 35.59 | 36.62 |
| 390 | PM 2:35 | 32.86 | 35.12 | 36.62 |
| 391 | PM 3:07 | 32.39 | 35.12 | 36.98 |
| 392 | PM 3:42 | 32.97 | 35.12 | 36.88 |
| 393 | PM 4:10 | 31.72 | 34.88 | 36.9 |
| 394 | PM 4:39 | 31.82 | 34.67 | 36.62 |
| 395 | PM 5:16 | 32.87 | 35.07 | 36.84 |
| 396 | PM 5:30 | 32.62 | 35.03 | 36.92 |
| 397 | PM 6:06 | 32.31 | 35.15 | 37.04 |
| 398 | PM 6:44 | 33.57 | 35.3 | 36.7 |
| 399 | PM 7:08 | 33.24 | 35.45 | 36.84 |
| 400 | PM 7:50 | 33 | 35.57 | 36.72 |
| 401 | PM 8:10 | 33.97 | 36.02 | 37.14 |

FIG. 16

| B | C | D | E | F | G |
|---|---|---|---|---|---|
| Measure time | Seq. | | Total | Outer Temp | Skin Temp |
| AM 8:18 | 0 | – | 608 | 30.35 | 32.31 |
| AM 8:19 | 1 | – | 608 | 30.21 | 32.37 |
| AM 8:20 | 2 | – | 608 | 30.42 | 32.49 |
| AM 8:21 | 3 | – | 608 | 30.51 | 32.58 |
| AM 8:22 | 4 | – | 608 | 30.34 | 32.68 |
| AM 8:23 | 5 | – | 608 | 30.2 | 32.76 |
| AM 8:24 | 6 | – | 608 | 30.23 | 32.82 |
| AM 8:25 | 7 | – | 608 | 30.35 | 32.88 |
| AM 8:26 | 8 | – | 608 | 30.43 | 32.93 |
| AM 8:27 | 9 | – | 608 | 30.38 | 32.97 |
| AM 8:28 | 10 | – | 608 | 30.31 | 33.05 |
| AM 8:29 | 11 | – | 608 | 30.51 | 33.13 |
| AM 8:30 | 12 | – | 608 | 30.96 | 33.2 |
| AM 8:31 | 13 | – | 608 | 30.81 | 33.24 |
| AM 8:32 | 14 | – | 608 | 30.95 | 33.32 |
| AM 8:33 | 15 | – | 608 | 30.69 | 33.4 |
| AM 8:34 | 16 | – | 608 | 29.92 | 33.46 |
| AM 8:35 | 17 | – | 608 | 29 | 33.41 |
| AM 8:36 | 18 | – | 608 | 29.64 | 33.4 |
| AM 8:37 | 19 | – | 608 | 29.42 | 33.35 |
| AM 8:38 | 20 | – | 608 | 29.07 | 33.31 |
| AM 8:39 | 21 | – | 608 | 30.04 | 33.37 |
| AM 8:40 | 22 | – | 608 | 30.49 | 33.42 |
| AM 8:41 | 23 | – | 608 | 30.67 | 33.46 |
| AM 8:42 | 24 | – | 608 | 30.6 | 33.51 |
| AM 8:43 | 25 | – | 608 | 30.93 | 33.55 |
| AM 8:44 | 26 | – | 608 | 31.39 | 33.61 |
| AM 8:45 | 27 | – | 608 | 28.98 | 33.58 |
| AM 8:46 | 28 | – | 608 | 28.4 | 33.44 |
| AM 8:47 | 29 | – | 608 | 28.57 | 33.34 |
| AM 8:48 | 30 | – | 608 | 29.71 | 33.31 |
| AM 8:49 | 31 | – | 608 | 28.92 | 33.33 |

External temperature processing (delay: 2min): 30.49−29.42=1.07

Skin temperature processing 33.51−33.37=0.14

FIG. 17

| B | C | D | E | F | G |
|---|---|---|---|---|---|
| Measure time | Seq. | | Total | Outer Temp | Skin Temp |
| AM 8:18 | 0 | – | 608 | 30.35 | 32.31 |
| AM 8:19 | 1 | – | 608 | 30.21 | 32.37 |
| AM 8:20 | 2 | – | 608 | 30.42 | 32.49 |
| AM 8:21 | 3 | – | 608 | 30.51 | 32.58 |
| AM 8:22 | 4 | – | 608 | 30.34 | 32.68 |
| AM 8:23 | 5 | – | 608 | 30.2 | 32.76 |
| AM 8:24 | 6 | – | 608 | 30.23 | 32.82 |
| AM 8:25 | 7 | – | 608 | 30.35 | 32.88 |
| AM 8:26 | 8 | – | 608 | 30.43 | 32.93 |
| AM 8:27 | 9 | – | 608 | 30.38 | 32.97 |
| AM 8:28 | 10 | – | 608 | 30.31 | 33.05 |
| AM 8:29 | 11 | – | 608 | 30.51 | 33.13 |
| AM 8:30 | 12 | – | 608 | 30.96 | 33.2 |
| AM 8:31 | 13 | – | 608 | 30.81 | 33.24 |
| AM 8:32 | 14 | – | 608 | 30.95 | 33.32 |
| AM 8:33 | 15 | – | 608 | 30.69 | 33.4 |
| AM 8:34 | 16 | – | 608 | 29.92 | 33.46 |
| AM 8:35 | 17 | – | 608 | 29 | 33.41 |
| AM 8:36 | 18 | – | 608 | 29.64 | 33.4 |
| AM 8:37 | 19 | – | 608 | 29.42 | 33.35 |
| AM 8:38 | 20 | – | 608 | 29.07 | 33.31 |
| AM 8:39 | 21 | – | 608 | 30.04 | 33.37 |
| AM 8:40 | 22 | – | 608 | 30.49 | 33.42 |
| AM 8:41 | 23 | – | 608 | 30.67 | 33.46 |
| AM 8:42 | 24 | – | 608 | 30.6 | 33.51 |
| AM 8:43 | 25 | – | 608 | 30.93 | 33.55 |
| AM 8:44 | 26 | – | 608 | 31.39 | 33.61 |
| AM 8:45 | 27 | – | 608 | 28.98 | 33.58 |
| AM 8:46 | 28 | – | 608 | 28.4 | 33.44 |
| AM 8:47 | 29 | – | 608 | 28.57 | 33.34 |
| AM 8:48 | 30 | – | 608 | 29.71 | 33.31 |
| AM 8:49 | 31 | – | 608 | 28.92 | 33.33 |
| | | | | | |

Processing of difference in skin temperature(T2): 33.46–33.31=0.15

Processing of change of difference in skin temperature(T=T1–T2): 0.14–0.15=0.01

Processing of difference in skin temperature(T1): 33.51–33.37=0.14

BODY TEMPERATURE ESTIMATION SYSTEM AND METHOD BASED ON ONE-CHANNEL TEMPERATURE SENSOR

CROSS-REFERENCE TO RELATED APPLICATION

The present application relates to a concurrently-filed U.S. patent application Ser. No. 18/053,906, entitled "BODY TEMPERATURE ESTIMATION SYSTEM AND METHOD CONSIDERING MOVEMENTS OF TARGET PERSON AND CHANGES IN EXTERNAL TEMPERATURE," which is incorporated herein in its entirety by reference.

TECHNICAL FIELD

The present disclosure relates to a body temperature estimation technology, and more particularly, to a system and method for estimating the body temperature of a target person in consideration of changes in the space temperature when continuously measuring the body temperature.

BACKGROUND

Recently, in the medical industry, efforts to create new types of medical devices or medical services by convergence of information and communications technologies (ICT) are expanding. For example, research is being conducted to collect and analyze patient's bio-signals in real time by attaching sensors of various uses and types to the patient and utilize the patient's biometric information for treatment of the patient.

In the biometric information, body temperature is the most basic diagnostic information and is an index that reflects various physiological changes. Temperature measurement is mandatory for most diseases. Recently, the importance of measuring the body temperature has been further emphasized due to the influence of COVID-19.

SUMMARY

The present disclosure provides a body temperature estimation system and method based on a one-channel temperature sensor for estimating the body temperature of a target person in consideration of a change in the space temperature or a change in the skin temperature according to a change in the space temperature when continuously measuring the body temperature.

According to the present disclosure, a body temperature estimation system continuously estimating a body temperature of a target person may include a temperature measurement unit attached to a skin of the target person and measuring a skin temperature at regular intervals; and a body temperature estimation unit estimating a current body temperature, based on an average body temperature measured at the regular intervals and the skin temperature received from the temperature measurement unit, by reflecting the average body temperature, the skin temperature, a difference value (h) of the skin temperature, and a change amount (h') of the skin temperature difference value.

The body temperature estimation unit may estimate a primary body temperature by correlation modeling between the average body temperature and the skin temperature.

The body temperature estimation unit may estimate a secondary body temperature by correlation modeling between the average body temperature, the primary body temperature, and the skin temperature difference value (h). The skin temperature difference value (h) is a difference value ($h=t_i-t_{i+j}$) between a skin temperature ($t_i$) at a current time and a skin temperature ($t_{i+j}$) before a first predetermined time from the current time, and The body temperature estimation unit may estimate the current body temperature by correlation modeling between the average body temperature, the secondary body temperature, and the change amount (h') of the skin temperature difference value. The change amount (h') of the skin temperature difference value is a difference value ($h'=T_1-T_2$) between a skin temperature difference value ($T_1$) based on the current time and a skin temperature difference value ($T_2$) based on a time before a second predetermined time from the current time.

The correlation may be modeled using MATLAB.

The average body temperature may be a value obtained by arithmetic average of body temperatures measured by a plurality of commercial thermometers.

The interval may be 1 minute, the first predetermined time may be 3 minutes, and the second predetermined time may be 1 minute.

The primary body temperature may be modeled with a quadratic function.

According to the present disclosure, a wearable temperature patch attached to a target person's skin and continuously estimating a body temperature may include a base film; a skin temperature sensor installed on the base film, being in contact with the target person's skin, and measuring a skin temperature at regular intervals; and a controller installed on the base film, receiving the measured skin temperature from the skin temperature sensor, and estimating a current body temperature, based on an average body temperature measured at the regular intervals and the received skin temperature, by reflecting the average body temperature, the skin temperature, a difference value (h) of the skin temperature, and a change amount (h') of the skin temperature difference value.

According to the present disclosure, a body temperature estimation system continuously estimating a body temperature of a target person may include a wearable temperature patch attached to a skin of the target person and continuously estimating the body temperature; and a management terminal receiving the estimated body temperature of the target person from the wearable temperature patch.

According to the present disclosure, a body temperature estimation method may include receiving, by a body temperature estimation unit, a skin temperature of a target person from a temperature measurement unit attached to a skin of the target person; and estimating, by the body temperature estimation unit, a current body temperature, based on an average body temperature measured at the regular intervals and the skin temperature received from the temperature measurement unit, by reflecting the average body temperature, the skin temperature, a difference value (h) of the skin temperature, and a change amount (h') of the skin temperature difference value.

According to the present disclosure, it is possible to more accurately estimate the body temperature of the target person in consideration of the temperature change of the space where the target person is located. That is, when the body temperature is continuously measured, the body temperature of the target person can be more accurately estimated by considering the change in the skin temperature (one-channel temperature) according to the change in the space temperature.

Therefore, since it is possible to correct the body temperature measurement error due to a sudden temperature change in the external environment, it is expected that more accurate and continuous body temperature measurement will be possible and the use of wearable temperature patches attachable to the skin will be expanded.

In addition, the wearable temperature patch according to the present invention is a wearable type that can be attached to the skin of a target person and enables continuous body temperature measurement in daily life, so it is expected to be used for medical staff to determine the diagnosis of an infectious disease through a more accurate long-term continuous temperature measurement record during social chaos such as the recent COVID-19 epidemic.

BRIEF DESCRIPTION OF THE DRAWINGS

FIG. 8 is a flowchart illustrating a body temperature estimation method using the body temperature estimation system according to the present disclosure.

FIGS. 9 to 14 are diagrams illustrating body temperature estimation methods according to a comparative example and embodiments;

FIG. 9 is a block diagram illustrating a body temperature estimation method according to a comparative example;

FIG. 10 is a block diagram illustrating a body temperature estimation method according to a first embodiment;

FIG. 11 is a block diagram illustrating a body temperature estimation method according to a second embodiment;

FIG. 12 is a block diagram illustrating a body temperature estimation method according to a third embodiment;

FIG. 13 is a block diagram illustrating a body temperature estimation method according to a fourth embodiment; and FIG. 14 is a block diagram illustrating a body temperature estimation method according to a fifth embodiment.

FIG. 15 is a table illustrating a dataset including external temperature, skin temperature, and average body temperature measured for 30 target persons.

FIG. 16 is a view illustrating an example of processing the external temperature and the skin temperature at the body temperature estimation step according to FIG. 13.

FIG. 17 is a view illustrating an example of processing the skin temperature at the body temperature estimation step according to FIG. 14.

DETAILED DESCRIPTION

Figures 1, 2:
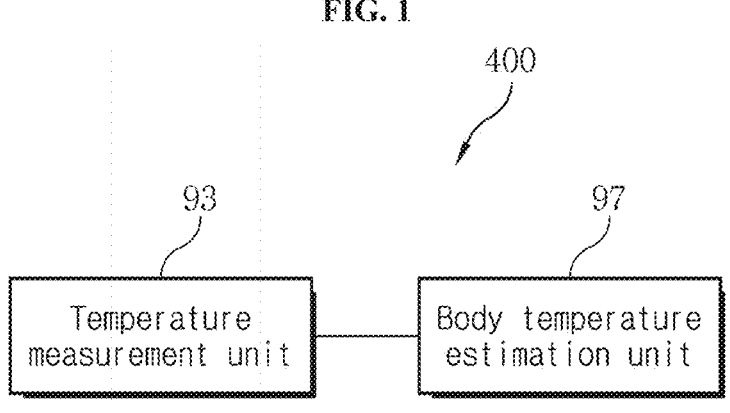
FIG. 1 is a block diagram illustrating a body temperature estimation system according to the present disclosure.
FIG. 2 is a block diagram illustrating a body temperature estimation system according to an embodiment of the present disclosure.

In the case that a target person is a patient, the existing body temperature measurement method is a regular check method in which a nurse visits a hospital room at a certain time to measure and record the patient's body temperature. Recently, research and attempts to measure the body temperature by using a medical patch attached to human skin are being actively conducted. This method is to automatically measure and record the body temperature for a long period of time through the medical patch without the patient's reluctance, so it can minimize the discomfort of patients due to body temperature measurement and greatly reduce the work intensity of nurses caused by regular check. This is expected to enable smart and efficient medical services to be provided to patients.

However, when the body temperature is measured over a long period of time in an environment in which the target person lives with the medical patch attached to the skin, the temperature of a space in which the target person is located often affects the measured external temperature. That is, when the space temperature is rapidly changed, the external temperature also greatly changes, and thus the accuracy of body temperature estimated (measured) through the medical patch is inevitably lowered.

Now, embodiments of the present disclosure will be described in detail with reference to the accompanying drawings.

However, in the following description and the accompanying drawings, well known techniques may not be described or illustrated in detail to avoid obscuring the subject matter of the present disclosure. Through the drawings, the same or similar reference numerals denote corresponding features consistently.

The terms and words used in the following description, drawings and claims are not limited to the bibliographical meanings thereof and are merely used by the inventor to enable a clear and consistent understanding of the disclosure. Thus, it will be apparent to those skilled in the art that the following description about various embodiments of the present disclosure is provided for illustration purpose only and not for the purpose of limiting the disclosure as defined by the appended claims and their equivalents.

[Body Temperature Estimation System]

FIG. 1 is a block diagram illustrating a body temperature estimation system according to the present disclosure.

Referring to FIG. 1, a body temperature estimation system 400 according to the present disclosure is a system for estimating the current body temperature through correlation modeling between the measured body temperature and at least one of the measured skin temperature and the measured external temperature in providing the body temperature of a target person over a long period of time. That is, the body temperature estimation system 400 is a system for estimating the body temperature of a target person in consideration of a sudden change in the external temperature.

The body temperature estimation system 400 includes a temperature measurement unit 93 and a body temperature estimation unit 97.

The temperature measurement unit 93 is attached to the skin of a target person and continuously measures the skin temperature and the external temperature at regular intervals. In this case, the regular interval may be several minutes, for example, one minute. The temperature measurement unit 93 time-synchronizes the measured skin temperature and the measured external temperature and outputs them to the body temperature estimation unit 97.

The temperature measurement unit 93 may further include a body part thermometer for measuring the body temperature of the target person required for modeling of a body temperature estimation model through correlation modeling.

As the body part thermometer, a commercial thermometer may be used. In order to reduce an error in the body temperature measurement process, the body temperature may be measured using a plurality of commercial thermometers.

The body temperature estimation unit 97 receives the skin temperature and the external temperature from the temperature measurement unit 93 and estimates the current body temperature using the received skin temperature and the received external temperature. That is, the body temperature estimation unit 97 performs modeling of a body temperature estimation model for estimating the current body temperature and, when at least one of the skin temperature and the external temperature is input from the temperature measurement unit 93, estimates the current body temperature by using the body temperature estimation model. The body temperature estimation model may be calculated by modeling a correlation between the measured body temperature and at least one of the measured skin temperature and the measured external temperature. The measured body temperature may be an average body temperature obtained by arithmetic average of body temperatures measured by a plurality of commercial thermometers. The correlation may use MATLAB.

The temperature measurement unit 93 is attached to the skin and measures the skin temperature and the external temperature at regular intervals. The temperature measurement unit 93 time-synchronizes the measured skin temperature and the measured external temperature and outputs them to the body temperature estimation unit 97.

The temperature measurement unit 93 may be implemented as a wearable temperature patch of a patch type that can be attached to the skin. The temperature measurement unit 93 measures the skin temperature through one surface attached to the skin, and measures the external temperature through the other surface facing the outside opposite to the skin.

The external temperature refers to a temperature (T2) acting on the skin by external heat-affecting factors (T1), such as sunlight, solar heat, outdoor temperature, heating and cooling facilities in a building, clothing, and bedding, which thermally affect the skin by the external environment. That is, the external temperature is not defined as a spatial representative temperature in terms of architecture, but is defined as a space temperature between the skin and the clothes worn by the target person. It may be considered to measure the spatial representative temperature in terms of architecture in real time and apply it to the body temperature estimation system 400, but this is not competitive in terms of cost and system configuration. Moreover, the temperature of a space between the clothes and the skin after the architectural external heat effect is filtered by the clothes is a key part influencing the estimated body temperature of the present disclosure.

The skin temperature is a body temperature detected from the skin in which the external temperature by the external heat-affecting factors is reflected. Therefore, it is preferable that the temperature measurement unit 93 measures the external temperature at an upper point on a position where the skin temperature is measured.

The body temperature estimation unit 97 estimates the body temperature of the target person, based on at least one of the skin temperature and the external temperature received from the temperature measurement unit 93. The body temperature estimation unit 97 estimates the body temperature in consideration of thermal effects in a section where a sudden temperature change occurs in a space where the target person is located.

The body temperature estimation unit 97 may correct the current body temperature as follows.

First, the body temperature estimation unit 97 may estimate the primary body temperature through correlation modeling between the average body temperature and the skin temperature, and then estimate the current body temperature by reflecting the primary body temperature, a difference value of the skin temperature, and a difference value of the external temperature. In this case, the primary body temperature is estimated by modeling with a linear function.

Second, the body temperature estimation unit 97 may estimate the primary body temperature through correlation modeling between the average body temperature and the skin temperature, and then estimate the current body temperature by reflecting the primary body temperature, a difference value of the skin temperature, and a difference value of the external temperature. In this case, the primary body temperature is estimated by modeling with a quadratic function.

Third, the body temperature estimation unit 97 may estimate the primary body temperature through correlation modeling between the average body temperature and the skin temperature, and then estimate the current body temperature by reflecting the primary body temperature and a difference value of the skin temperature. In this case, the primary body temperature is estimated by modeling with a quadratic function.

Fourth, the body temperature estimation unit 97 may estimate the primary body temperature through correlation modeling between the average body temperature and the skin temperature, and then estimate the current body temperature by reflecting the primary body temperature, a difference value of the skin temperature, and a delayed difference value of the external temperature. In this case, the primary body temperature is estimated by modeling with a quadratic function.

As such, the body temperature estimation unit 97 may estimate the current body temperature through correlation modeling between the average body temperature, the skin temperature, and the external temperature. When estimating the secondary body temperature, the body temperature estimation unit 97 reflects a delayed difference value of the external temperature. The reason for reflecting the delayed difference value of the external temperature will be described later.

Fifth, the body temperature estimation unit 97 may estimate the primary body temperature through correlation modeling between the average body temperature and the skin temperature. Next, the body temperature estimation unit 97 may estimate the secondary body temperature by reflecting the primary body temperature and a difference value of the skin temperature. In addition, the body temperature estimation unit 97 may estimate the current body temperature by reflecting the secondary body temperature and the amount of change (difference value) in the skin temperature difference value. In this case, the primary body temperature is estimated by modeling with a quadratic function.

As such, the body temperature estimation unit 97 may estimate the current body temperature through correlation modeling between the average body temperature and the skin temperature. That is, the body temperature estimation unit 97 may estimate the current body temperature, based on the average body temperature measured at the same interval as the skin temperature measurement interval and the skin temperature received from the temperature measurement unit 93. In addition, the body temperature estimation unit 97 may estimate the current body temperature by reflecting the average body temperature, the skin temperature, the skin temperature difference value, and the amount of change in the skin temperature difference value.

Specifically, the body temperature estimation unit 97 estimates the primary body temperature by correlation modeling between the average body temperature and the skin temperature. Next, the body temperature estimation unit 97 estimates the secondary body temperature through correlation modeling between the average body temperature, the primary body temperature, and the skin temperature difference value. In addition, the body temperature estimation unit 97 estimates the current body temperature by correlation modeling between the average body temperature, the secondary body temperature, and the amount of change in the skin temperature difference value. In this case, the amount of change in the skin temperature difference value is a difference value between the skin temperature difference value based on the current time and the skin temperature difference value based on the time before a second predetermined time with respect to the current time. The skin temperature difference value is a difference value between the current skin temperature and the skin temperature before a first predetermined time based on the current time.

The above-described body temperature estimation system 400 according to the present disclosure may be implemented in embodiments shown in FIGS. 2 to 7, but this is not a limitation.

FIG. 2 is a block diagram illustrating a body temperature estimation system 400 according to an embodiment of the present disclosure.

Referring to FIG. 2, the temperature estimation system 400 according to this embodiment includes a wearable temperature patch 100 and a management terminal 200. In addition, the temperature estimation system 400 according to this embodiment may further include a body part thermometer 300.

The body part thermometer 300 measures the body temperature of a target person's body part and outputs it. The body part thermometer 300 measures the body temperature of one of chest, forehead, armpit, ear, and earlobe. The body part thermometer 300 may be a commercial thermometer.

The body part thermometer 300 is used to model the correlation for body temperature estimation according to this embodiment, and to check the accuracy of the body temperature estimated from the modeled correlation with the body temperature measured by the body part thermometer 300. In order to model the correlation for body temperature estimation, it is preferable to use the body part thermometer 300 capable of accurately measuring the body temperature. In this embodiment, the body temperature is measured using a plurality of commercial thermometers as the body part thermometer 300, and the average body temperature obtained by arithmetic average of the measured body temperatures is used. By using the average body temperature, the possibility of errors occurring by using a specific commercial thermometer is minimized.

The wearable temperature patch 100 is attached to the skin of the target person and continuously measures the skin temperature and the external temperature at regular intervals. The wearable temperature patch 100 may time-synchronize the skin temperature and the external temperature and output them. The wearable temperature patch 100 may be a flexible temperature sensor module implemented as a flexible patch type. The wearable temperature patch 100 may perform the function of the above-described temperature measurement unit.

In addition, the management terminal 200 estimates the body temperature of the target person, based on the skin temperature and external temperature received from the wearable temperature patch 100. That is, the management terminal 200 receives the skin temperature and external temperature from the wearable temperature patch 100. In addition, the management terminal 200 may estimate the current body temperature by using at least one of the measured skin temperature and external temperature. The management terminal 200 is a communication terminal used by a manager, and may be, for example, a PC, a smartphone, a notebook computer, a tablet PC, a dedicated terminal, a server, or the like. The management terminal 200 may perform the function of the above-described body temperature estimation unit.

In this embodiment, the body part thermometer 300, the wearable temperature patch 100, and the management terminal 200 are capable of performing communication in a wireless communication scheme. As the wireless communication scheme, a short-range wireless communication scheme may be used. As the short-range wireless communication scheme, Bluetooth, Bluetooth Low Energy (BLE), WiFi, Zigbee, Near Field Communication (NFC), or the like may be used.

Meanwhile, in this embodiment, the management terminal 200 is described as performing the function of the body temperature estimation unit, but the disclosure is not limited thereto.

For example, the wearable temperature patch 100 may include the temperature measurement unit and the body temperature estimation unit. That is, the wearable temperature patch 100 is attached to the skin of the target person and continuously measures the skin temperature and the external temperature at regular intervals. The wearable temperature patch 100 time-synchronizes the skin temperature and the external temperature. The wearable temperature patch 100 may estimate the current body temperature by using at least one of the measured skin temperature and external temperature. In addition, the management terminal 200 may receive the skin temperature, the external temperature, or the estimated body temperature from the wearable temperature patch 100 and output or manage it.

Hereinafter, the wearable temperature patch 100 according to this embodiment will be described in detail with reference to FIGS. 3 to 6.

Figure 3:
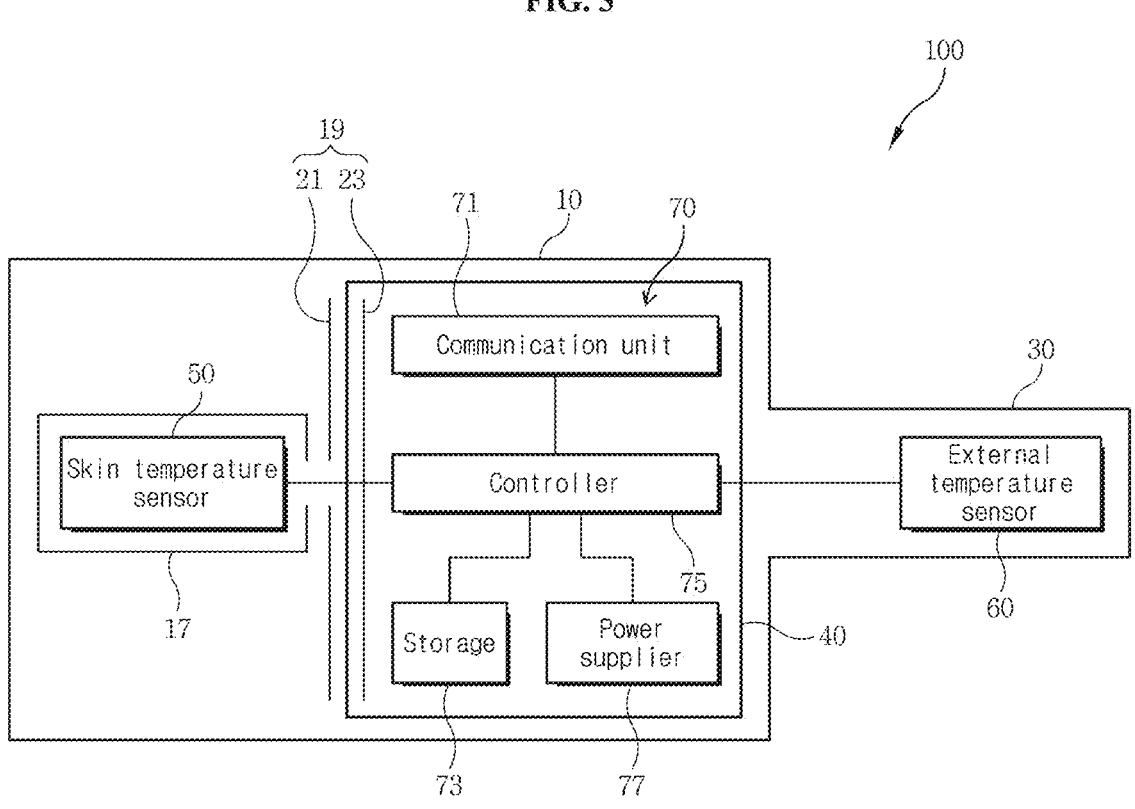
FIG. 3 is a block diagram illustrating the wearable temperature patch of FIG. 2.

FIG. 3 is a block diagram illustrating the wearable temperature patch 100 of FIG. 2.

Referring to FIG. 3, the wearable temperature patch 100 according to this embodiment includes flexible base films 10 and 30 and a skin temperature sensor 50. The base films 10 and 30 have a mounting region 15 in which the skin temperature sensor 50 is mounted, and also have heat conduction blocking slots 17 and 19 formed for blocking heat conduction to the mounting region 15. The skin temperature sensor 50 is mounted in the mounting region 15 of the base films 10 and 30, is in contact with the skin, and measures the skin temperature. In addition, the wearable temperature patch 100 according to this embodiment may further include an external temperature sensor 60, a ground layer 40, and a heat-generating element 70.

By forming the heat conduction blocking slots 17 and 19 around the skin temperature sensor 50, the wearable temperature patch 100 according to this embodiment can block heat conduction to the skin temperature sensor 50 through the base films 10 and 30. That is, it is possible to reduce the influence of internal heat-affecting factors with the heat conduction blocking slots 17 and 19.

The internal heat-affecting factors will be described. In a printed circuit board including the base films 10 and 30, heat generated from the skin around the skin temperature sensor 50 and heat generated during the operation of the heat-generating element 70 are conducted to the skin temperature sensor 50 through the ground layer 40 or the electrode layer in the printed circuit board, thereby affecting the measured body temperature.

Therefore, in order to block such heat effects due to the internal heat-affecting factor, the heat conduction blocking slots 17 and 19 are formed in this embodiment.

The heat conduction blocking slots 17 and 19 may include at least one of a guard slot 17 formed in the base film 10 along the circumference of the skin temperature sensor 50, and a boundary slot 19 formed near a boundary between the mounting region 15 where the skin temperature sensor 50 is mounted, and a region where the ground layer 40 is formed. The boundary slot 19 includes at least one of a first boundary slot 21 formed in the base film 10 and a second boundary slot 23 formed in the ground layer 40. In this embodiment, the guard slot 17 and the boundary slot 19 are formed together, and the first and second boundary slots 21 and 23 are formed together.

The base films 10 and 30 include a first base film 10 and a second base film 30. The second base film 30 is connected to the first base film 10 and bent over the first base film 10.

The skin temperature sensor 50, the ground layer 40, and the heat-generating element 70 are formed on the first base film 10. In addition, the external temperature sensor 60 is formed on the second base film 30.

The skin temperature sensor 50 is mounted on one side of the first base film 10.

The ground layer 40 is formed on the first base film 10 spaced apart from the mounting region 15 where the skin temperature sensor 50 is mounted.

The heat-generating element 70 is formed on the first base film 10 spaced apart from the mounting region 15 on which the skin temperature sensor 50 is mounted. In this case, the heat-generating element 70 may be formed in a region where the ground layer 40 is formed.

The heat-generating element 70 refers to an element included in the wearable temperature patch 100 and capable of affecting the skin temperature sensor 50 according to an internal heat-affecting factor. The heat-generating element 70 may include a communication unit 71, a storage 73, a controller 75, and a power supplier 77.

The communication unit 71 performs communication with the management terminal 200. The communication unit 71 may use a short-range wireless communication scheme as a communication scheme with the management terminal 200.

The storage 73 stores the skin temperature measured by the skin temperature sensor 50 and/or the external temperature measured by the external temperature sensor 60.

The controller 75 is a microprocessor that controls the overall operation of the wearable temperature patch 100. The controller 75 transmits the temperature measured by the skin temperature sensor 50 and the external temperature sensor 60 or the temperature stored in storage 73 to the management terminal 200 through the communication unit 71.

The power supplier 77 supplies power required for operations to the skin temperature sensor 50, the communication unit 71, the storage 73, and the controller 75. The power supplier 77 is an electrical energy storage device that can be charged and discharged multiple times, and may include, for example, at least one of a secondary battery and a super capacitor. The power supplier 77 may include an energy harvesting unit that collects energy around the wearable temperature patch 100, such as a body temperature or a wireless signal, and generates electrical energy.

Figure 4:
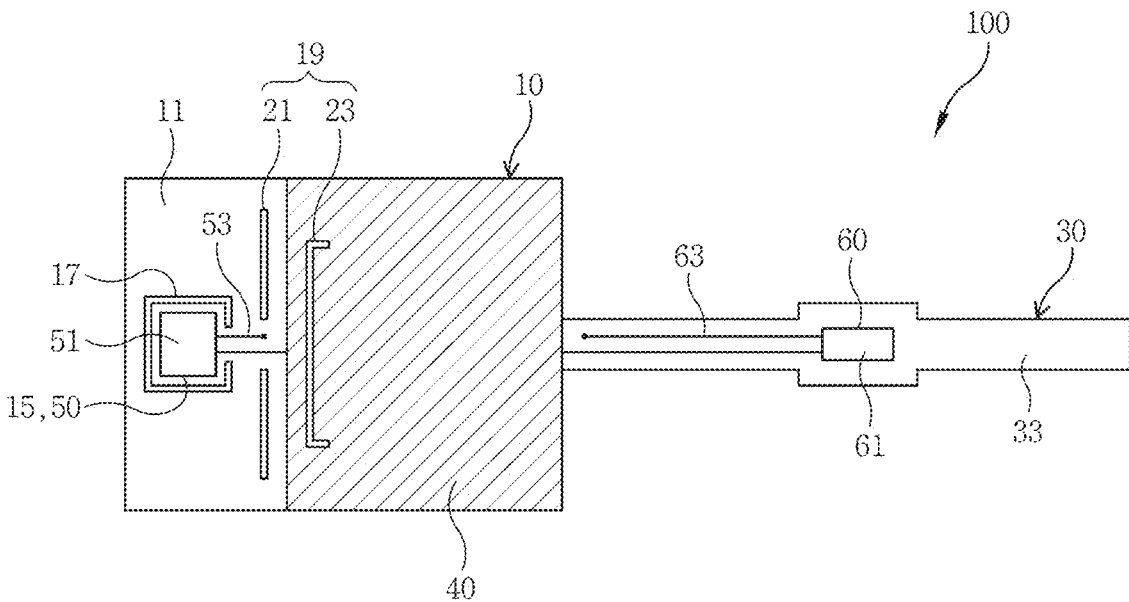
FIG. 4 is a plan view illustrating a lower surface of the wearable temperature patch according to an embodiment of the present disclosure.
Figure 5:
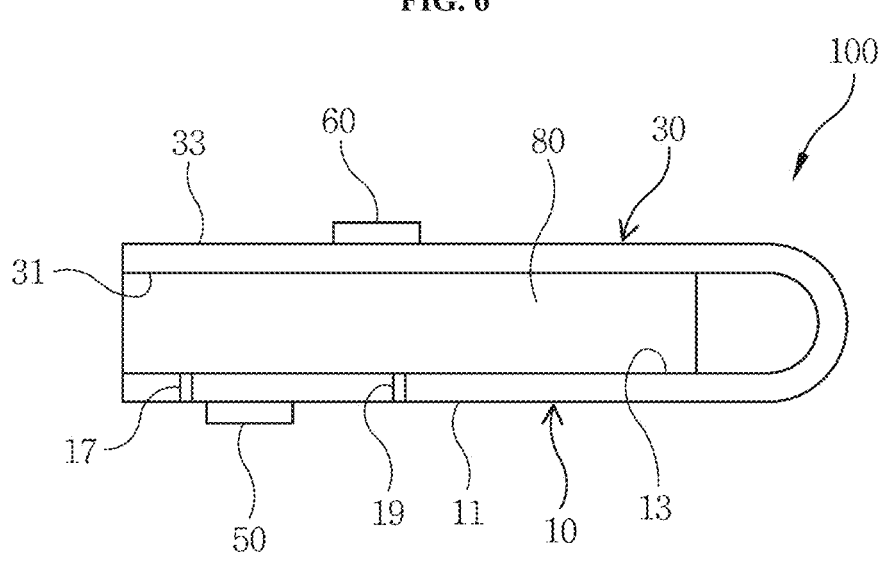
FIG. 5 is a plan view illustrating an upper surface of the wearable temperature patch according to an embodiment of the present disclosure.
Figure 6:
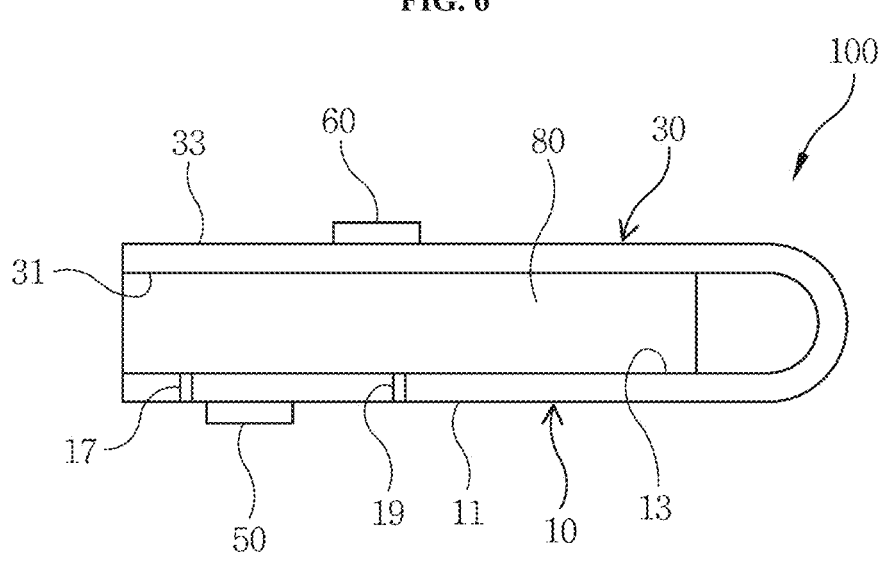
FIG. 6 is a cross-sectional view illustrating the wearable temperature patch, in a state where a second base film is bent over a first base film, according to an embodiment of the present disclosure.

FIG. 4 is a plan view illustrating a lower surface of the wearable temperature patch 100 according to an embodiment of the present disclosure. FIG. 5 is a plan view illustrating an upper surface of the wearable temperature patch 100 according to an embodiment of the present disclosure. FIG. 6 is a cross-sectional view illustrating the wearable temperature patch 100, in a state where a second base film 30 is bent over a first base film 10, according to an embodiment of the present disclosure.

Referring to FIGS. 4 to 6, the wearable temperature patch 100 according to this embodiment includes the flexible base films 10 and 30 and the skin temperature sensor 50 and may further include the external temperature sensor 60, the ground layer 40, the heat-generating element 70, and a protective layer 80.

The base films 10 and 30 are insulating films made of a flexible plastic material. The material of the base films 10 and 30 may include, but is not limited to, polyimide, polyethersulphone (PES), polyacrylate (PAR), polyetherimide (PEI), polyethylene naphthalate (PEN), polyethylene terephthalate (PET), polyphenylene sulfide (PPS), polyallylate, polycarbonate (PC), cellulose triacetate (CTA), or cellulose acetate propinonate (CAP).

The base films 10 and 30 include the first base film 10 and the second base film 30. Each of the first and second base films 10 and 30 has an upper surface 13 or 33 and a lower surface 11 or 31 opposite to the upper surface 13 or 33. Because the second base film 30 is bent and positioned over the upper surface 13 of the first base film 10, the lower surface 11 of the first base film 10 and the upper surface 33 of the second base film 30 are coplanar and the upper surface 13 of the first base film 10 and the lower surface 31 of the second base film 30 are coplanar in the plan views of FIGS. 4 and 5.

The skin temperature sensor 50 and the ground layer 40 are formed on the lower surface 11 of the first base film 10. The skin temperature sensor 50 and the ground layer 40 are formed to be spaced apart from each other. The heat-generating element 70 is mounted on the upper surface 13 of the first base film 10.

The external temperature sensor 60 is formed on the upper surface 33 of the second base film 30. The second base film 30 is formed to be narrower than the first base film 10 so that it can be easily bent with respect to the first base film 10 and positioned over the first base film 10.

When the second base film 30 is bent with respect to the first base film 10, the lower surface 11 of the first base film 10 on which the skin temperature sensor 50 is mounted faces the skin, and the external temperature sensor 60 faces the outside. That is, after the lower surface 11 of the first base film 10 and the upper surface 33 of the second base film 30 are positioned to face downward, the second base film 30 is bent so that its lower surface 31 is positioned over the upper surface 13 of the first base film 10.

The ground layer 40 is formed on the lower surface 11 of the first base film 10, but this is not a limitation. For example, the ground layer 40 may be formed inside the first base film 10.

The skin temperature sensor 50 is a temperature sensor of resistance film type based on a platinum material, and includes an internal sensor 51 and an internal electrode 53. The internal sensor 51 measures the body temperature (skin temperature) of a contacted skin. The internal electrode 53 is connected to the internal sensor 51 and transmits the measured skin temperature to the storage 73 or the controller 75. The internal electrode 53 may be formed of a plurality of lines, one of the plurality of lines may be connected to the ground layer 40, and the other may be connected to the storage 73 or the controller 75 to which the measured skin temperature is transmitted.

The guard slot 17 is formed to penetrate the first base film 10 around the skin temperature sensor 50. The guard slot 17 is formed to surround the skin temperature sensor 50 and is not formed in a portion where the internal electrode 53 is formed. That is, the guard slot 17 is formed to surround the internal sensor 51 except for a portion where the internal electrode 53 connected to the internal sensor 51 is drawn out.

The boundary slot 19 includes the first boundary slot 21 and the second boundary slot 23. The first boundary slot 21 may be formed near both sides of the internal electrode 53. The second boundary slot 23 may be formed in the ground layer 40 in a form that covers the controller 75 in a direction of the skin temperature sensor 50. The second boundary slot 23 is formed to penetrate the ground layer 40 and the first base film 10.

As described above, by forming the guard slot 17 and/or the boundary slot 19 around the skin temperature sensor 50, the wearable temperature patch 100 according to this embodiment can block heat conduction to the skin temperature sensor 50 through the base films 10 and 30. That is, it is possible to reduce the influence of internal heat-affecting factors by the guard slot 17 and/or the boundary slot 19 at the skin temperature measured by the skin temperature sensor 50.

The heat-generating element 70 is mounted on the upper surface 13 of the first base film 10. The heat-generating element 70 is mounted on the upper surface 13 of the first base film 10 opposite to the lower surface 11 of the first base film 10 on which the ground layer 40 is formed.

The protective layer 80 protects the heat-generating element 70 from the external environment. The protective layer 80 may be formed by laminating a protective film of a plastic resin on the upper surface 13 of the first base film 10 where the heat-generating element 70 is mounted. Alternatively, the protective layer 80 may be formed by coating or molding a liquid plastic resin. As a material of the protective layer 80, a plastic material or a nonwoven fabric capable of providing flexibility to the first base film 10 may be used.

The second base film 30 bent over the first base film 10 may be attached on the protective layer 80.

The external temperature sensor 60 is mounted on the upper surface 33 of the second base substrate. The external temperature sensor 60 is a temperature sensor of resistance film type based on a platinum material, and includes an external sensor 61 and an external electrode 63. The external sensor 61 measures the external temperature applied to the wearable temperature patch 100 from the opposite side to the skin. The external electrode 63 is connected to the external sensor 61 and transmits the measured external temperature to the storage 73 or the controller 75. The external electrode 63 may be formed of a plurality of lines, one of the plurality of lines may be connected to the ground layer 40, and the other may be connected to the storage 73 or the controller 75 to which the measured external temperature is transmitted.

As such, the external temperature sensor 60 measures the external temperature according to the external heat-affecting factor.

Figure 7:
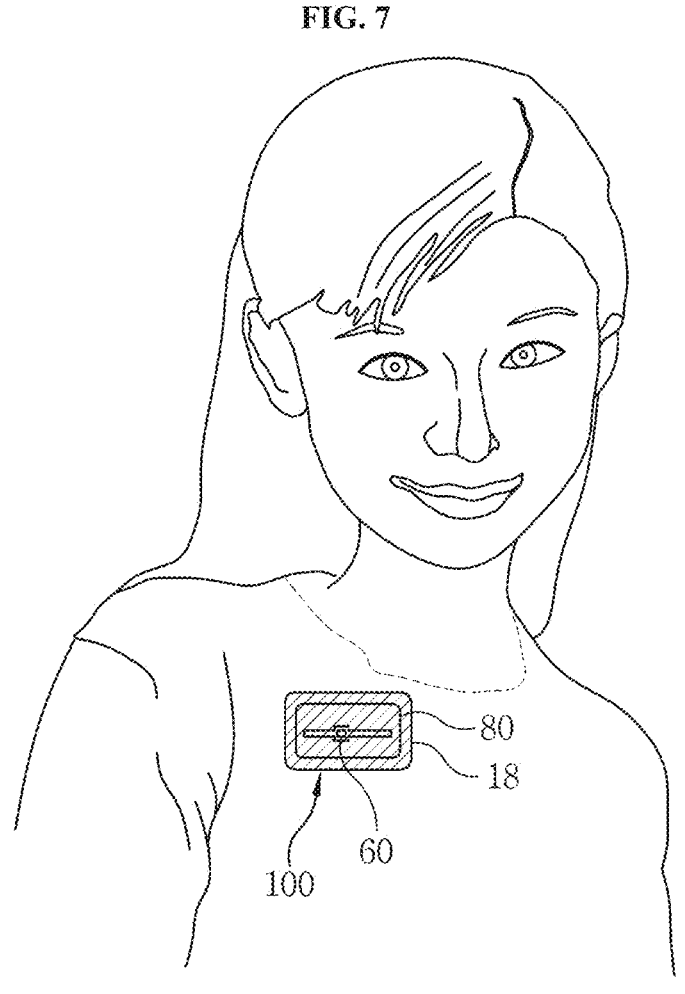
FIG. 7 is a view illustrating a wearable temperature patch attached to an upper part of the chest according to an embodiment of the present disclosure.

FIG. 7 is a view illustrating a wearable temperature patch 100 attached to an upper part of the chest according to an embodiment of the present disclosure.

Referring to FIG. 7, the wearable temperature patch 100 according to this embodiment may be attached to various body parts of a target person using an attachment pad 18. FIG. 7 shows an example in which the wearable temperature patch 100 is attached to an upper part of the chest by the attachment pad 18. The attachment pad 18 may be an adhesive tape made of flexible plastic, paper, or non-woven fabric.

The wearable temperature patch 100 is attached so that the skin temperature sensor 50 faces the skin of an upper part of the chest. The wearable temperature patch 100 is attached so that the external temperature sensor 60 is positioned just below the attachment pad 18 and faces the outside of an upper part of the chest.

Although FIG. 7 shows an example in which the wearable temperature patch 100 is not directly exposed to the external environment by the top, it may be directly exposed to the external environment depending on the use environment.

[Body Temperature Estimation Method]

Now, the body temperature estimation method using the body temperature estimation system according to this embodiment will be described with reference to FIGS. 2 and 8 to 16.

FIG. 8 is a flowchart illustrating a body temperature estimation method using the body temperature estimation system according to the present disclosure.

Referring to FIGS. 2 and 8, at step S10, the wearable temperature patch 100 attached to the skin of the target person measures the external temperature and the skin temperature at regular intervals. The body part thermometer 300 measures the body temperature of the target person at regular intervals.

Then, at step S30, the management terminal 200 estimates the current body temperature through correlation modeling with at least one of the skin temperature and external temperature measured by the wearable temperature patch 100 based on the body temperature measured by the body part thermometer 300.

That is, when the body temperature estimation model is modeled through the correlation modeling, the management terminal 200 estimates the current body temperature by using at least one of the skin temperature and external temperature received from the wearable temperature patch 100.

Now, the method for estimating body temperature according to the present disclosure will be described in detail through a comparative example and embodiments shown in FIGS. 9 to 14. FIGS. 9 to 14 are diagrams illustrating body temperature estimation methods according to a comparative example and embodiments.

FIG. 9 is a block diagram illustrating a body temperature estimation method according to a comparative example.

Referring to FIG. 9, the body temperature estimation method according to the comparative example is to estimate the current body temperature through correlation modeling with skin temperature, external temperature, and body temperature.

The body temperature estimation method according to the comparative example may be useful as a method for estimating the current body temperature in a general environment in which a sudden change in space temperature does not occur, that is, in a space in which constant temperature is maintained.

However, when a sudden change in the space temperature occurs, the external temperature measured by the wearable temperature patch 100 changes rapidly, but a change in the skin temperature is not large. Therefore, the body temperature estimation method according to the comparative example has a problem in that the accuracy of the estimated current body temperature is low. That is, when the temperature of an indoor space changes rapidly due to the movement from the outdoor to the indoor or the operation of an air conditioner or heater, the body temperature estimated by the body temperature estimation method according to the comparative example using the correlation between the external temperature and skin temperature measured in a section where the sudden temperature change occurs has a large error from the actually measured body temperature.

It is judged that the cause of the error between the estimated body temperature and the measured body temperature as described above is that information about a temperature environment from which a target person with the wearable temperature patch 100 attached has moved is not reflected. That is, it is judged that if past information of the target person is reflected in the body temperature estimation, the body temperature estimation error due to spatial movement can be reduced.

Accordingly, the first to fifth embodiments of the present disclosure provide a body temperature estimation method considering past information of a target person. The first, second, and fourth embodiments provide a body temperature estimation method using the external temperature and the skin temperature. The third and fifth embodiments provide a body temperature estimation method using the skin temperature. Because of using only the skin temperature, the third and fifth embodiments relate to a body temperature estimation method based on a one-channel temperature sensor. Because of using both the skin temperature and the external temperature, the first, second, and fourth embodiments relate to a body temperature estimation method based on a two-channel temperature sensor.

First Embodiment

Figure 10:
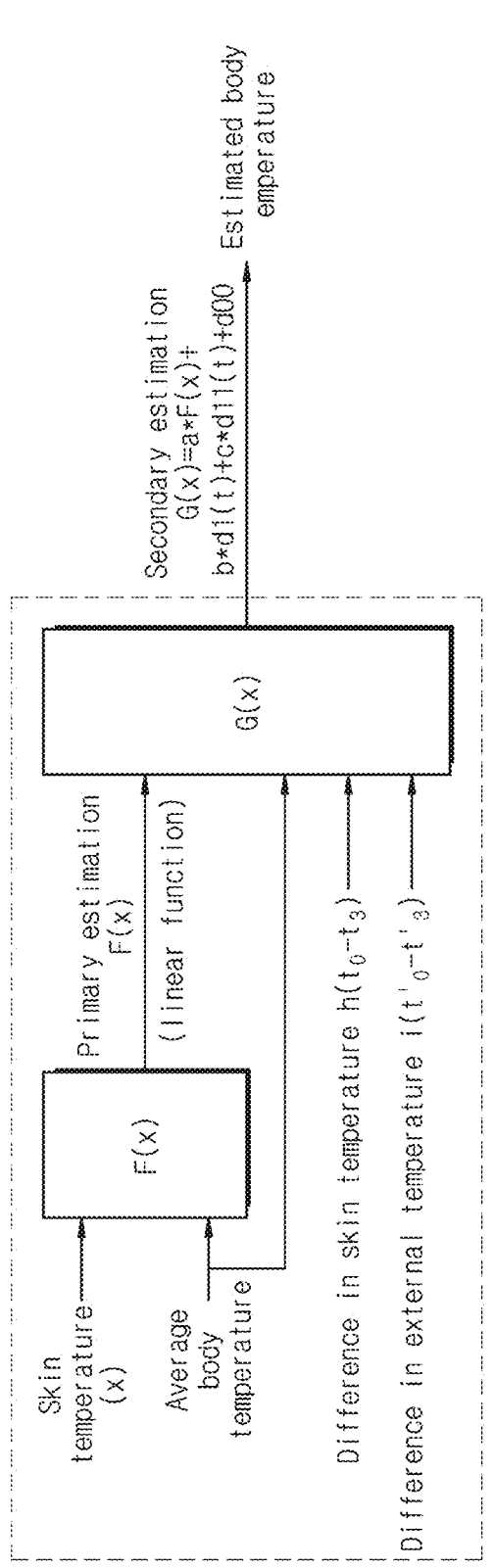

FIG. 10 is a block diagram illustrating a body temperature estimation method according to a first embodiment.

Referring to FIG. 10, the body temperature estimation method according to the first embodiment includes estimating a primary body temperature and estimating a secondary body temperature using the primary body temperature.

First, the body temperature estimation unit estimates the primary body temperature (F(x)) through correlation modeling between the average body temperature and the skin temperature (x). In this case, the primary body temperature (F(x)) is estimated by modeling with a linear function.

In addition, the body temperature estimation unit estimates the current body temperature, which is the secondary body temperature (G(x)), by reflecting the primary body temperature (F(x)), a difference value (h) of the skin temperature, and a difference value (i) of the external temperature.

The difference value (h) of the skin temperature is a difference value between the current skin temperature $(t_i)$ and the skin temperature $(t_{i+j})$ before the first predetermined time (j) from the current time as shown in Equation 1 below.

$$h=t_i-t_{i+j} \qquad \text{[Equation 1]}$$

The first predetermined time may be set within 5 minutes, and preferably may be set between 1 minute and 5 minutes.

The reason for setting the first predetermined time within 5 minutes is as follows. It can be seen that when a sudden change in the space temperature occurs, the external temperature is changed for about 15 minutes and then recovered to the external temperature before the sudden change in the space temperature occurs. In particular, the external temperature changes rapidly within the first 5 minutes and is then recovered to the external temperature before the sudden space temperature change occurs within 10 minutes thereafter.

Therefore, in order to reflect a sudden change in the external temperature when estimating the body temperature, it is preferable to determine the first predetermined time within 5 minutes. For example, the first predetermined time may be 3 minutes. The difference value of the skin temperature is defined as a difference value $(t_0-t_3)$ between the current skin temperature $(t_0)$ and the skin temperature $(t_3)$ before 3 minutes from the current time.

The external temperature difference value (i) is set in the same way as the skin temperature difference value (h).

That is, the difference value (i) of the external temperature is, as shown in Equation 2 below, a difference value between the current external temperature $(t'_i)$ and the external temperature $(t'_{i+j})$ before the first predetermined time (j) from the current time.

$$i=t'_i-t'_{i+j} \qquad \text{[Equation 2]}$$

Therefore, in order to reflect a sudden change in the external temperature when estimating the body temperature, it is preferable to determine the first predetermined time within 5 minutes. For example, the first predetermined time may be 3 minutes. The difference value of the external temperature is defined as a difference value $(t'_0-t'_3)$ between the current external temperature $(t'_0)$ and the external temperature $(t'_3)$ before 3 minutes from the current time.

In addition, the current body temperature (G(x)) can be estimated by Equation 3 below.

$$G(x)=a*F(x)+b*d1(t)+c*d11(t)+d00 \qquad \text{[Equation 3]}$$

a: weight of primary body temperature
d1(t): difference value of skin temperature
b: weight of skin temperature
d11(t): difference value of external temperature
c: weight of external temperature
d00: constant The body temperature estimation unit determines a, b, c, and d00 in Equation 3 through correlation modeling based on the average body temperature.

By determining a, b, c, and d00 through correlation modeling, the body temperature estimation unit can estimate the current body temperature (G(x)) using Equation 3 when the external temperature and the skin temperature are measured with the wearable temperature patch.

Second Embodiment

FIG. 11 is a block diagram illustrating a body temperature estimation method according to a second embodiment.

Referring to FIG. 11, the body temperature estimation method according to the second embodiment is performed in the same manner as in the first embodiment. However, in the second embodiment, the primary body temperature is estimated by modeling with a quadratic function.

Third Embodiment

Figure 12:
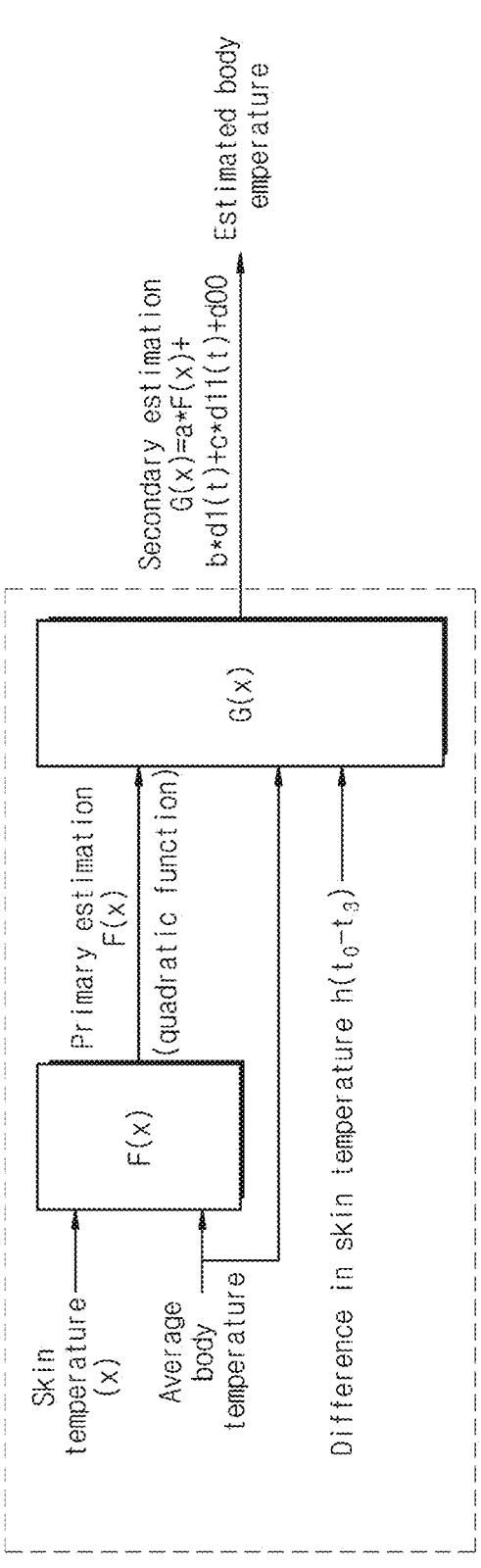

FIG. 12 is a block diagram illustrating a body temperature estimation method according to a third embodiment.

Referring to FIG. 12, the body temperature estimation method according to the third embodiment includes estimating a primary body temperature and estimating a secondary body temperature using the primary body temperature.

First, the body temperature estimation unit estimates the primary body temperature (F(x)) through correlation modeling between the average body temperature and the skin temperature (x). In this case, the primary body temperature (F(x)) is estimated by modeling with a quadratic function.

In addition, the body temperature estimation unit estimates the current body temperature, which is the secondary body temperature (G(x)), by reflecting the primary body temperature (F(x)) and a difference value (h) of the skin temperature.

The secondary body temperature (G(x)) can be estimated by Equation 4 below.

$$G(x)=a*F(x)+b*d1(t)+c*d11(t)+d00 \qquad \text{[Equation 4]}$$

a: weight of primary body temperature
d1(t): difference value of skin temperature
b: weight of skin temperature
d11(t): difference value of external temperature
c: weight of external temperature
d00: constant The body temperature estimation unit determines a, b, and d00 in Equation 4 through correlation modeling based on the average body temperature. Because the external temperature is not reflected, c=0.

By determining a, b, and d00 through correlation modeling, the body temperature estimation unit can estimate the current body temperature (G(x)) using Equation 4 when the skin temperature is measured with the wearable temperature patch.

Fourth Embodiment

Figure 13:
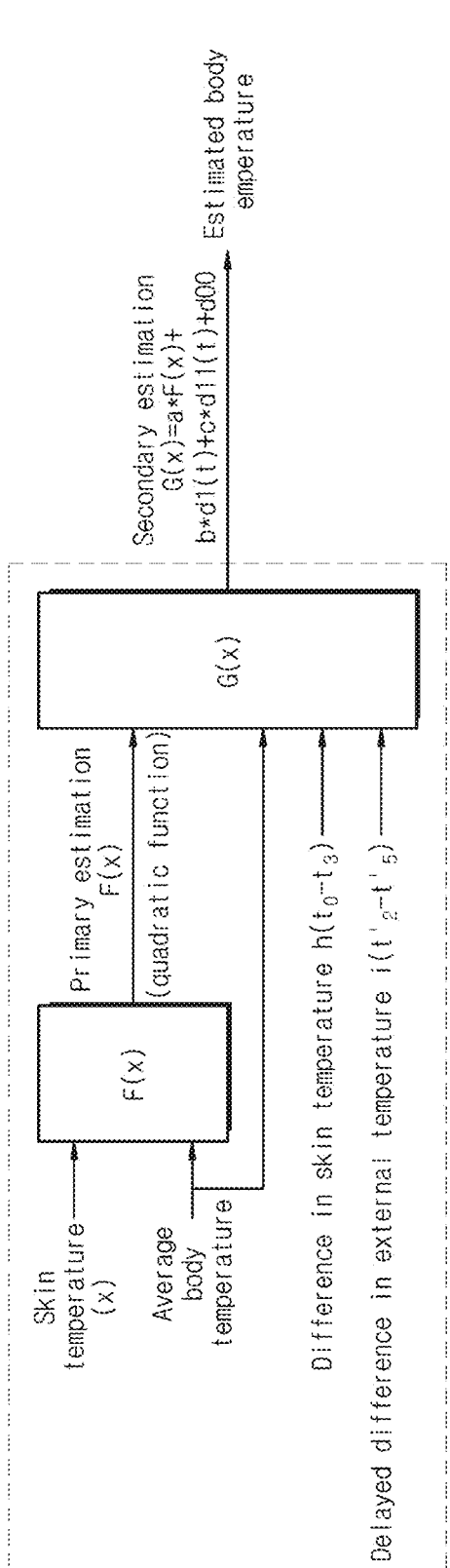

FIG. 13 is a block diagram illustrating a body temperature estimation method according to a fourth embodiment.

Referring to FIG. 13, the body temperature estimation method according to the fourth embodiment includes estimating a primary body temperature and estimating a secondary body temperature using the primary body temperature.

First, the body temperature estimation unit estimates the primary body temperature (F(x)) through correlation modeling between the average body temperature and the skin temperature (x). In this case, the primary body temperature (F(x)) is estimated by modeling with a quadratic function.

In addition, the body temperature estimation unit estimates the current body temperature, which is the secondary body temperature (G(x)), by reflecting the primary body temperature (F(x)), a difference value (h) of the skin temperature, and a delayed difference value (i) of the external temperature.

Here, the difference value of the skin temperature can be calculated by Equation 1.

The delayed difference value of the external temperature can be calculated by Equation 5.

$$i=t'_{i+k}-t'_{i+j+k} \qquad \text{[Equation 5]}$$

That is, as the delayed difference value of the external temperature, a difference value between the current external temperature (t'_i) and the external temperature (t'_{i+j}) before the first predetermined time (j) from the current time is calculated, but the difference value of the external temperature is calculated by delaying the second predetermined time (k). The second predetermined time (k) may be a time delayed by 2 minutes from the current time.

For example, the difference value of the skin temperature is defined as the difference value ($t_0-t_3$) between the current skin temperature ($t_0$) and the skin temperature ($t_3$) before 3 minutes from the current time. In addition, the delayed difference value of the external temperature is defined as ($t'_2-t'_5$) when a time delayed by 2 minutes from the current time is reflected.

The reason for calculating the delayed difference value of the external temperature is as follows.

Because the wearable temperature patch itself delays heat transfer, it takes time for the external temperature to affect the skin temperature.

This time delay can be confirmed through the Pearson correlation coefficient between the external temperature and the skin temperature. According to the Pearson correlation coefficient, it can be seen that the correlation between the external temperature measured by the external temperature sensor and the skin temperature measured by the skin temperature sensor is significantly increased when a time delay of 2 minutes is reflected. This means that after the heat passing through the clothing by the external heat effect is measured by the external temperature sensor, it takes time for this heat to pass through the wearable temperature patch and transmit the heat effect to the skin temperature sensor. That is, this means that it takes about 2 minutes for the external temperature to pass through the wearable temperature patch and affect the skin.

In addition, the current body temperature (G(x)) can be estimated by Equation 6 below.

$$G(x)=a*F(x)+b*d1(t)+c*d11(t)+d00 \qquad \text{[Equation 6]}$$

a: weight of primary body temperature
d1(t): difference value of skin temperature
b: weight of skin temperature
d11(t): delayed difference value of external temperature
c: weight of external temperature
d00: constant The body temperature estimation unit determines a, b, c, and d00 in Equation 6 through correlation modeling based on the average body temperature.

By determining a, b, c, and d00 through correlation modeling, the body temperature estimation unit can estimate the current body temperature (G(x)) using Equation 6 when the external temperature and the skin temperature are measured with the wearable temperature patch.

Fifth Embodiment

FIG. 14 is a block diagram illustrating a body temperature estimation method according to a fifth embodiment.

Referring to FIG. 14, the body temperature estimation method according to the fifth embodiment includes estimating a primary body temperature, estimating a secondary body temperature using the primary body temperature, and estimating a tertiary body temperature using the secondary body temperature. The body temperature estimation method according to the fifth embodiment uses the skin temperature when estimating the primary to tertiary body temperatures.

First, the body temperature estimation unit estimates the primary body temperature (F(x)) through correlation modeling between the average body temperature and the skin temperature (x). In this case, the primary body temperature (F(x)) is estimated by modeling with a quadratic function.

Next, the body temperature estimation unit estimates the secondary body temperature (G(x)) by reflecting the primary body temperature (F(x)) and a difference value (h) of the skin temperature. Here, the secondary body temperature (G(x)) can be calculated by Equation 7 in the same manner as in the third embodiment. The difference value (h) of the skin temperature can be calculated by Equation 1.

$$G(x)=a*F(x)+b*d1(t)+c*d2(t)+d00 \qquad \text{[Equation 7]}$$

a: weight of primary body temperature
d1(t): difference value of skin temperature
b: weight of skin temperature
d2(t): difference value of external temperature
c: weight of external temperature
d00: constant The body temperature estimation unit determines a, b, and d00 in Equation 7 through correlation modeling based on the average body temperature. Because the external temperature is not reflected, c=0.

By determining a, b, and d00 through correlation modeling, the body temperature estimation unit estimates the secondary body temperature (G(x)) using Equation 7 when the skin temperature is measured with the wearable temperature patch.

In addition, the body temperature estimation unit estimates the tertiary body temperature (H(x)) by reflecting the secondary body temperature (G(x)) and the amount (h') of change in the difference value of the skin temperature.

Here, the change amount (h') of the skin temperature difference value can be calculated by Equation 8 below.

$$H'=T_1-T_2 \qquad \text{[Equation 8]}$$

$T_1$: difference value of skin temperature based on current time
$T_2$: difference value of skin temperature based on previous time That is, the change amount (h') of the skin temperature difference value is a difference between the skin temperature difference value ($T_1$) based on the current time and the skin temperature difference value ($T_2$) based on the time before the second predetermined time from the current time.

$T_1$ and $T_2$ can be calculated by Equation 1. In this case, the first predetermined time may be set within 5 minutes, and preferably may be set between 1 minute and 5 minutes. The second predetermined time may be set shorter than the first predetermined time. For example, when the first predetermined time is 3 minutes, the second predetermined time may be 1 minute.

The tertiary body temperature (H(x)) is calculated using Equation 9.

$$H(x)=a*F(x)+b*d11(t)+c*d22(t)+d00 \qquad \text{[Equation 9]}$$

a: weight of primary body temperature
d1(t): change amount of skin temperature difference value
b: weight of skin temperature
d22(t): difference value of external temperature
c: weight of external temperature
d00: constant The body temperature estimation unit determines a, b, and d00 in Equation 3 through correlation modeling based on the average body temperature. Because the external temperature is not reflected, c=0.

By determining a, b, and d00 through correlation modeling, the body temperature estimation unit estimates the current body temperature (H(x)) using Equation 9 when the skin temperature is measured with the wearable temperature patch.

The above-described body temperature estimation methods according to embodiments were confirmed through specific experimental examples shown in FIGS. 15 to 17. The wearable temperature patch 100 according to the embodiment was attached to the upper part of the chest of the target person as shown in FIG. 7. The wearable temperature patch 100 measures the skin temperature and external temperature generated in the process of the target person moving naturally in various spaces during daily life.

The wearable temperature patch 100 according to the embodiment may measure and store the external temperature and the skin temperature at the same time and may measure the external temperature and the skin temperature at regular intervals of 1 minute. After the body temperatures are measured three times at the same measurement point using a plurality of commercial thermometers, the management terminal calculates the average body temperature by arithmetic average of the measured body temperatures.

FIG. 15 is a table illustrating a dataset including external temperature, skin temperature, and average body temperature measured for 30 target persons.

Referring to FIG. 15, the wearable temperature patch according to the embodiment was attached to 30 people to measure the external temperature and the skin temperature, and the management terminal obtained 400 datasets by time-synchronizing with the average body temperature measured with a commercial thermometer.

Using the datasets of FIG. 15, the current body temperature was estimated through the body temperature estimation methods according to the comparative example and the first to fifth embodiments. The accuracy of the body temperature estimation method according to the present disclosure was confirmed by comparing the estimated body temperature with the average body temperature.

In the comparative example, the current body temperature was estimated through correlation modeling with skin temperature, external temperature, and body temperature.

The body temperature estimation method according to the comparative example may be usefully used as a method for estimating the current body temperature in a general environment in which a sudden change in space temperature does not occur, that is, in a space in which constant temperature is maintained.

However, when a sudden change in the space temperature occurs, the external temperature measured by the wearable temperature patch 100 changes rapidly, but a change in the skin temperature is not large. Therefore, the body temperature estimation method according to the comparative example has a problem in that the accuracy of the estimated current body temperature is low.

In all the first to fifth embodiments, the primary body temperature was estimated through correlation modeling between the average body temperature and the skin temperature (x). The primary body temperature was modeled with a linear function in the first embodiment and modeled with a quadratic function in the second to fifth embodiments.

In the first and second embodiments, the current body temperature was estimated using the two-channel temperature sensor. In this case, when estimating the current body temperature which is the secondary body temperature, each of the difference value of the skin temperature and the difference value of the external temperature was calculated as a difference between the temperature measured at the current time and the temperature measured before 3 minutes from the current time.

In the third embodiment, the current body temperature, which is the secondary body temperature, was estimated using the one-channel temperature sensor (skin temperature sensor). The current body temperature, which is the secondary body temperature, was estimated by reflecting the primary body temperature and the difference value of the skin temperature. In this case, the difference value of the skin temperature was calculated as a difference between the skin temperature measured at the current time and the skin temperature measured before 3 minutes from the current time.

In the fourth embodiment, the current body temperature, which is the secondary body temperature, was estimated by reflecting the primary body temperature, the difference value of the skin temperature, and the delayed difference value of the external temperature.

The difference value of the skin temperature and the delayed difference value of the external temperature may be calculated as shown in FIG. 16. FIG. 16 is a view illustrating an example of processing the external temperature and the skin temperature at the body temperature estimation step according to FIG. 13.

In the fourth embodiment, the difference value of the skin temperature was calculated as a difference between the skin temperature measured at the current time and the skin temperature measured before 3 minutes from the current time.

In the fourth embodiment, the delayed difference value of the external temperature was calculated as a difference between the external temperature measured at a time delayed by 2 minutes from the current time and the external temperature measured before 3 minutes from the time delayed by 2 minutes. For example, if the current time is 8:42 am, the difference value of the skin temperature is calculated as a difference between the first skin temperature (8:42 am) and the second skin temperature (8:39 am). The delayed difference value of the external temperature is calculated as a difference between the first external temperature (8:40 am) and the second external temperature (8:37 am).

In the fifth embodiment, the current body temperature, which is the tertiary body temperature, was estimated using the one-channel temperature sensor (skin temperature sensor).

The difference value of the skin temperature and the amount of change in the difference value of the skin temperature can be calculated as shown in FIG. 17. FIG. 17 is a view illustrating an example of processing the skin temperature at the body temperature estimation step according to FIG. 14.

The amount of change ($h'=T$) in the difference value of the skin temperature was calculated as follows.

The difference value ($T_1$) of the skin temperature based on the current time is calculated as a difference ($t_0-t_3$) between the skin temperature ($t_0$) measured at the current time and the skin temperature ($t_3$) measured before 3 minutes from the current time. For example, if the current time is 8:42 am, the difference value ($T_1$) of the skin temperature is calculated as a difference between the first skin temperature (8:42 am) and the second skin temperature (8:39 am).

The difference value ($T_2$) of the skin temperature based on the previous time is calculated as a difference ($t_1-t_4$) between the skin temperature ($t_1$) measured before 1 minute from the current time and the skin temperature ($t_4$) measured before 3 minutes from the 1 minute prior time. For example, if the current time is 8:42 am, the difference value ($T_2$) of the skin temperature based on the time one minute before is calculated as a difference between the first skin temperature (8:41 am) and the second skin temperature (8:38 am).

In addition, the amount of change ($h'=T$) in the difference value of the skin temperature is calculated as ($T_1-T_2$).

Comparing the current body temperatures estimated by the body temperature estimation methods according to the comparative example and the first to fifth embodiments, it is as shown in Tables 1 to 3. Table 1 shows the case where a difference between the average body temperature measured by a commercial thermometer and the body temperature estimated by the body temperature estimation method is 0.3 degrees or more as the error occurrence range. Table 2 shows the case of 0.4 degree or more, and Table 3 shows the case of 0.5 degree or more. Here, the coincidence rate (%) was calculated as [(datasets−number of errors)/data set]×100.

TABLE 1

|  | Comparative example | $1^{st}$ embodiment | $2^{nd}$ embodiment | $3^{rd}$ embodiment | $4^{th}$ embodiment | $5^{th}$ embodiment |
|---|---|---|---|---|---|---|
| Number of errors | 71 | 66 | 67 | 72 | 67 | 71 |
| Datasets | 400 | 400 | 400 | 400 | 400 | 400 |
| Coincidence rate | 0.8225 | 0.835 | 0.825 | 0.82 | 0.8325 | 0.8225 |

TABLE 2

|  | Comparative example | $1^{st}$ embodiment | $2^{nd}$ embodiment | $3^{rd}$ embodiment | $4^{th}$ embodiment | $5^{th}$ embodiment |
|---|---|---|---|---|---|---|
| Number of errors | 33 | 34 | 35 | 33 | 34 | 32 |
| Datasets | 400 | 400 | 400 | 400 | 400 | 400 |
| Coincidence rate | 0.9175 | 0.915 | 0.9125 | 0.9175 | 0.915 | 0.92 |

TABLE 3

| | Comparative example | 1st embodiment | 2nd embodiment | 3rd embodiment | 4th embodiment | 5th embodiment |
|---|---|---|---|---|---|---|
| Number of errors | 16 | 15 | 16 | 15 | 14 | 13 |
| Datasets | 400 | 400 | 400 | 400 | 400 | 400 |
| Coincidence rate | 0.96 | 0.9625 | 0.96 | 0.9625 | 0.965 | 0.9675 |

Referring to Tables 1 to 3, it can be seen that the body temperature estimation methods according to the first to fifth embodiments have similar or improved coincidence rates than in the comparative example. Moreover, it can be confirmed that the fourth and fifth examples are capable of more accurate body temperature estimation than the comparative examples.

Among the body temperature estimation methods based on the two-channel temperature sensor, it can be seen that the fourth embodiment shows excellent performance. Moreover, the fourth embodiment exhibits better performance than the comparative example.

Among the body temperature estimation methods based on the one-channel temperature sensor, it can be seen that the fifth embodiment maintains excellent performance. Moreover, the body temperature estimation method based on the one-channel temperature sensor according to the fifth embodiment maintains excellent performance compared to the body temperature estimation methods according to the first to fourth embodiments and exhibits excellent performance in the error occurrence range of 0.5 degrees or more.

Meanwhile, although in this experimental example the body temperature estimation methods according to the present disclosure were modeled based on 400 datasets, more accurate body temperature estimation is possible when a dataset is added.

While the present disclosure has been particularly shown and described with reference to an exemplary embodiment thereof, it will be understood by those skilled in the art that various changes in form and details may be made therein without departing from the scope of the present disclosure as defined by the appended claims.

This work was supported by the Energy Demand Management Core Technology Development of the Korea Institute of Energy Technology Evaluation and Planning (KETEP) granted financial resource from the Ministry of Trade, Industry & Energy, Republic of Korea (No. 20212020900380).

What is claimed is:

1. A body temperature estimation system continuously estimating a body temperature of a target person, the system comprising:
a thermometer including a temperature sensor configured to be attached to a skin of the target person and configured to measure a skin temperature at regular intervals; and
a processor of a management terminal configured to estimate a current body temperature, based on an average body temperature measured at the regular intervals and the skin temperature received from the thermometer, by reflecting the average body temperature, the skin temperature, a skin temperature difference value (h) of the skin temperature, and a change amount (h') of the skin temperature difference value, wherein the skin temperature difference value (h) is obtained by using skin temperatures measured at different times, and
wherein the change amount (h') of the skin temperature difference value is obtained by using skin temperature difference values (h) obtained based on different reference times.

2. The body temperature estimation system of claim 1, wherein the processor is configured to:
estimate a primary body temperature by correlation modeling between the average body temperature and the skin temperature;
estimate a secondary body temperature by correlation modeling between the average body temperature, the primary body temperature, and the skin temperature difference value (h), wherein the skin temperature difference value (h) is a difference value ($h=t_i-t_{i+j}$) between a skin temperature ($t_i$) at a current time and a skin temperature ($t_{i+j}$) before a first predetermined time from the current time; and
estimate the current body temperature by correlation modeling between the average body temperature, the secondary body temperature, and the change amount (h') of the skin temperature difference value, wherein the change amount (h') of the skin temperature difference value is a difference value ($h'=T_1-T_2$) between a skin temperature difference value ($T_1$) based on the current time and a skin temperature difference value ($T_2$) based on a time before a second predetermined time from the current time.

3. The body temperature estimation system of claim 2, wherein the correlation is modeled using MATLAB.

4. The body temperature estimation system of claim 2, wherein the interval is 1 minute, the first predetermined time is 3 minutes, and the second predetermined time is 1 minute.

5. The body temperature estimation system of claim 2, wherein the primary body temperature is modeled with a quadratic function.

6. The body temperature estimation system of claim 1, wherein the average body temperature is a value obtained by arithmetic average of body temperatures measured by a plurality of commercial thermometers.

7. A wearable temperature patch attached to a target person's skin and continuously estimating a body temperature, comprising:
a base film;
a skin temperature sensor installed on the base film, configured to be in contact with the target person's skin, and configured to measure a skin temperature at regular intervals; and
a controller installed on the base film and configured to:
receive the measured skin temperature from the skin temperature sensor, and
estimate a current body temperature, based on an average body temperature measured at the regular intervals and the received skin temperature, by reflecting the average body temperature, the skin temperature, a skin temperature difference value (h) of the skin temperature, and a change amount (h') of the skin temperature difference value, wherein the skin temperature difference value (h) is obtained by using skin temperatures measured at different times, and wherein the change amount (h') of the skin temperature difference value is obtained by using skin temperature difference values (h) obtained based on different reference times.

8. The wearable temperature patch of claim 7, wherein the controller is configured to:

estimate a primary body temperature by correlation modeling between the average body temperature and the skin temperature;

estimate a secondary body temperature by correlation modeling between the average body temperature, the primary body temperature, and the skin temperature difference value (h), wherein the skin temperature difference value (h) is a difference value (h=ti−ti+j) between a skin temperature (ti) at a current time and a skin temperature (ti+j) before a first predetermined time from the current time; and estimate the current body temperature by correlation modeling between the average body temperature, the secondary body temperature, and the change amount (h') of the skin temperature difference value, wherein the change amount (h') of the skin temperature difference value is a difference value (h'=T1−T2) between a skin temperature difference value (T1) based on the current time and a skin temperature difference value (T2) based on a time before a second predetermined time from the current time.

9. A body temperature estimation system continuously estimating a body temperature of a target person, comprising:

a wearable temperature patch configured to be attached to a skin of the target person and configured to continuously estimate the body temperature; and a management terminal configured to receive the estimated body temperature of the target person from the wearable temperature patch, wherein the wearable temperature patch includes:

a base film;

a skin temperature sensor installed on the base film, being in contact with the target person's skin, and configured to measure a skin temperature at regular intervals; and a controller installed on the base film configured to receive the measured skin temperature from the skin temperature sensor, and estimate a current body temperature, based on an average body temperature measured at the regular intervals and the received skin temperature, by reflecting the average body temperature, the skin temperature, a skin temperature difference value (h) of the skin temperature, and a change amount (h') of the skin temperature difference value, wherein the skin temperature difference value (h) is obtained by using skin temperatures measured at different times, and wherein the change amount (h') of the skin temperature difference value is obtained by using skin temperature difference values (h) obtained based on different reference times.

10. The body temperature estimation system of claim 9, wherein the controller is configured to:

estimate a primary body temperature by correlation modeling between the average body temperature and the skin temperature;

estimate a secondary body temperature by correlation modeling between the average body temperature, the primary body temperature, and the skin temperature difference value (h), wherein the skin temperature difference value (h) is a difference value (h=ti−ti+j) between a skin temperature (ti) at a current time and a skin temperature (ti+j) before a first predetermined time from the current time; and estimate the current body temperature by correlation modeling between the average body temperature, the secondary body temperature, and the change amount (h') of the skin temperature difference value, wherein the change amount (h') of the skin temperature difference value is a difference value (h'=T1−T2) between a skin temperature difference value (T1) based on the current time and a skin temperature difference value (T2) based on a time before a second predetermined time from the current time.

11. A body temperature estimation method comprising:

receiving, by a processor of a management terminal, a skin temperature of a target person from a thermometer configured to be attached to a skin of the target person; and estimating, by the processor, a current body temperature, based on an average body temperature measured at the regular intervals and the skin temperature received from the thermometer, by reflecting the average body temperature, the skin temperature, a skin temperature difference value (h) of the skin temperature, and a change amount (h') of the skin temperature difference value, wherein the skin temperature difference value (h) is obtained by using skin temperatures measured at different times, and wherein the change amount (h') of the skin temperature difference value is obtained by using skin temperature difference values (h) obtained based on different reference times.

12. The body temperature estimation method of claim 11, wherein the estimating includes:

estimating, by the processor, a primary body temperature by correlation modeling between the average body temperature and the skin temperature;

estimating, by the processor, a secondary body temperature by correlation modeling between the average body temperature, the primary body temperature, and the skin temperature difference value (h);

estimating, by the processor, the current body temperature by correlation modeling between the average body temperature, the secondary body temperature, and the change amount (h') of the skin temperature difference value;

wherein the skin temperature difference value (h) is a difference value (h=ti−ti+j) between a skin temperature (ti) at a current time and a skin temperature (ti+j) before a first predetermined time from the current time; and wherein the change amount (h') of the skin temperature difference value is a difference value (h'=T1−T2) between a skin temperature difference value (T1) based on the current time and a skin temperature difference value (T2) based on a time before a second predetermined time from the current time.

* * * * *